United States Patent
Matuszewski et al.

(10) Patent No.: US 12,263,191 B2
(45) Date of Patent: Apr. 1, 2025

(54) MICRONIZED COMPOSITIONS FOR WOUND HEALING PREPARED FROM INTACT HUMAN AMNION-CHORION TISSUE HAVING AN INTACT INTERMEDIATE SPONGY LAYER POSITIONED THERE BETWEEN

(71) Applicant: BioStem Technologies, Inc., Pompano Beach, FL (US)

(72) Inventors: Jason V. Matuszewski, Boca Raton, FL (US); Wendy W. Weston, Coral Springs, FL (US)

(73) Assignee: BioStem Technologies, Inc., Pompano Beach, FL (US)

( * ) Notice: Subject to any disclaimer, the term of this patent is extended or adjusted under 35 U.S.C. 154(b) by 0 days.

(21) Appl. No.: 18/593,225

(22) Filed: Mar. 1, 2024

(65) Prior Publication Data
US 2024/0245731 A1    Jul. 25, 2024

Related U.S. Application Data

(63) Continuation of application No. PCT/US2023/026436, filed on Jun. 28, 2023.

(60) Provisional application No. 63/356,628, filed on Jun. 29, 2022, provisional application No. 63/391,032, filed on Jul. 21, 2022.

(51) Int. Cl.
| | | |
|---|---|---|
| *A61K 35/50* | (2015.01) | |
| *A61K 31/726* | (2006.01) | |
| *A61K 31/728* | (2006.01) | |
| *A61K 38/17* | (2006.01) | |
| *A61K 38/18* | (2006.01) | |
| *A61K 38/20* | (2006.01) | |
| *A61K 38/39* | (2006.01) | |
| *A61K 41/10* | (2020.01) | |

(52) U.S. Cl.
CPC ............ *A61K 35/50* (2013.01); *A61K 31/726* (2013.01); *A61K 31/728* (2013.01); *A61K 38/179* (2013.01); *A61K 38/1833* (2013.01); *A61K 38/2006* (2013.01); *A61K 38/39* (2013.01); *A61K 41/10* (2020.01)

(58) Field of Classification Search
CPC .................................................. A61K 35/50
See application file for complete search history.

(56) References Cited

U.S. PATENT DOCUMENTS

| | | |
|---|---|---|
| 6,933,326 B1 | 8/2005 | Griffey et al. |
| 8,357,403 B2 | 1/2013 | Daniel et al. |
| 8,372,437 B2 | 2/2013 | Daniel |
| 8,409,626 B2 | 4/2013 | Daniel et al. |
| 9,101,586 B2* | 8/2015 | Bader ............... A61K 47/32 |
| 10,105,397 B2* | 10/2018 | Morse ............... A61K 35/12 |
| 11,219,647 B2 | 1/2022 | Morse et al. |
| 2008/0069895 A1 | 3/2008 | Liu et al. |
| 2010/0143312 A1* | 6/2010 | Hariri ............... A61K 35/50 |
| | | 424/93.7 |
| 2016/0199417 A1 | 7/2016 | Werber et al. |
| 2016/0263280 A1* | 9/2016 | Harrell ............. A61L 27/3604 |
| 2017/0157295 A1 | 6/2017 | Daniel |
| 2019/0046585 A1 | 2/2019 | Morse et al. |

OTHER PUBLICATIONS

Roy, A. et al. ,"Intermediate layer contribution in placental membrane allografts", J. Tissue Eng Regen Med. 2020; 14:1126-1135. (Year: 2020).*
Lei, J. et al. "Identification of extracellular matrix components and biological factors in micronized dehydrated human amnion/chorion membrane", Adv Wound Care, Feb. 1, 2017; 6(2); 43-53. (Year: 2017).*
Intention to Grant for corresponding European Application No. 23744947.5; dated Jul. 16, 2024; (58 pages).
International Search Report (ISR) for PCT/US2023/26436 mailed Oct. 10, 2023 (3 pages).
Written Opinion (WO) for PCT/US2023/26436 mailed Oct. 10, 2023 (5 pages).
International Preliminary Report on Patentability issued for PCT/US2023/026436; issued Dec. 18, 2024 (6 Pages).
European Search Report issued for EP Pat. App. No. 24195379.3 dated Oct. 14, 2024 (10 pages).
Schoepf, Christoph: "The Tutoplast Process: A review of Efficacy", Zimmer Dental dated Jan. 1, 2008 (3 pages).
McQuilling et al., "Characterisation of dehydrated amnion chorion membranes and evaluation of fibroblast and keratinocyte responses in vitro", International Wound Journal, vol. 16, No. 3, dated Jun. 1, 2019, pp. 827-840.
Koob et al., "Properties of dehydrated human amnion/chorion composite grafts: Implications for wound repair and soft tissue regeneration", Journal of Biomedical Materials Research Part B: Applied Biomaterials, vol. 102, No. 6, dated Mar. 25, 2024, pp. 1353-1362.

* cited by examiner

*Primary Examiner* — Gina C Justice
(74) *Attorney, Agent, or Firm* — Shumaker, Loop & Kendrick, LLP

(57) ABSTRACT

A sterile micronized composition prepared from intact human placental tissue for wound healing. The sterile micronized composition includes micronized human amnion; micronized human chorion; and micronized human intermediate spongy layer. In certain aspects, the composition is prepared from intact placental tissue comprising a human amnion layer, human chorion layer, and an intact human intermediate spongy layer positioned between the human amnion layer and human chorion layer such that immediately before micronization the human amnion layer and the human chorion layer are not separated from one another.

21 Claims, 5 Drawing Sheets

MICRONIZED COMPOSITIONS FOR WOUND HEALING PREPARED FROM INTACT HUMAN AMNION-CHORION TISSUE HAVING AN INTACT INTERMEDIATE SPONGY LAYER POSITIONED THERE BETWEEN

TECHNICAL FIELD

The present invention relates generally to the field of compositions prepared from human placental tissue(s), and more particularly, to micronized or sterile micronized compositions for wound healing in subjects in need thereof that are prepared from intact human placental tissue (human amnion, human chorion, and a human intermediate spongy layer connected to one another and intact in cross-section).

BACKGROUND

The human placenta is an organ that develops in the uterus shortly after implantation of a fertilized human egg (forming an embryo), attaching the fertilized human egg to the wall of the uterus. The human placenta is composed of parenchyma, chorion, amnion and the umbilical cord, which connects to the fetus. During fetal development, the amnion and chorion fuse together to form the chorio-amniotic membrane that encases the amniotic fluid and the fetus. The fetal membrane's (amniotic sac) full thickness measures approximately 0.25 mm at term. This includes the layers of the innermost amnion and layers of the outer chorion.

In utero, the amnion is in direct contact with the amniotic fluid. Amnion has three layers, which contain type I and type III-VII collagen, and high concentrations of proteoglycans and glycoproteins along with fibronectin and laminin. The functions of the amniotic membrane include physical protection of the fetus, protection from bacterial infection, regulation of pH, and secretion of growth factors and other molecules. These serve antimicrobial and anti-inflammatory functions.

The chorion is the outer layer of the human placenta that is in contact with the mother's cells. It forms tail-like structures called the chorionic villi, which provide blood and nutrients from the mother to the baby. The amnion and chorion are separated by a jellylike matrix (chorionic fluid) until the two membranes "fuse" at 11-13 weeks post-conception. The chorion is 3-4 times thicker than the amnion and has three layers: the intermediate/reticular layer (contacts the amnion), the basement membrane, and the trophoblast layer. The reticular layer contains type I, type III, type IV, type V and type VI collagen. The basement membrane contains type IV collagen along with fibronectin and laminin.

In 1910, John Davis was the first to report the use of amnion membrane (AM or amnion) as a surgical material in skin transplantation. Davis showed that in skin grafting, amniotic membrane resulted in better outcomes than xenograft or cadaveric dressings (6). Since then, human amniotic membrane has been used in regenerative medicine due to its favorable biological and mechanical properties. Numerous applications benefit from these properties. For example, amnion membrane for management and treatment of skin burns and has been utilized in over 200 clinical trials. Similarly, amniotic membrane has shown potential advantageous outcomes when used for chronic wounds, urinary system issues, dental and oral treatments, ophthalmic indications and orthopedic treatments.

The human chorion by itself is not commonly used in medicine for regenerative applications, but the combination of amnion and chorion (AC) has been used in the field. Like AM, AC in various forms have been used for numerous applications.

The primary application for compositions that include both the human amnion and human chorion are wound healing. However, these compositions tend to be highly processed laminates that lose various endogenous growth factors found within the human placenta in vivo due to the extensive processing these compositions undergo. Moreover, these compositions have reduced and/or limited wound healing capabilities due to the loss of various endogenous growth factors during processing of these compositions. For example, U.S. Pat. Nos. 8,357,403, 8,372,437, 8,409,626, and U.S. patent application Ser. No. 17/097,350 each disclose various formulations in which the amnion is physically separated from the chorion and portions of the intermediate spongy layer positioned there between are partially lost during separation and/or are intentionally, completely removed during processing. Moreover, in each U.S. Pat. Nos. 8,357,403, 8,372,437, 8,409,626, and U.S. patent application Ser. No. 17/097,350 the separated amnion and/or the separated chorion are each further processed into laminates or are further micronized individually with a substantial portion of the intermediate sponge layer being at least partially and/or completely removed when compared to the human placenta in vivo. Thus, the compositions disclosed in U.S. Pat. Nos. 8,357,403, 8,372,437, 8,409,626, and U.S. patent application Ser. No. 17/097,350, and more particularly the growth factor profiles of those compositions, greatly differ when compared to the growth factor profiles of the human placenta in vivo and have reduced and/or limited wound healing capabilities due to the loss of various endogenous growth factors during processing of these compositions.

In addition to the above, various human placenta based compositions in the field of regenerative medicine utilize harsh processing techniques such as cryofracturing (generally described in Taylor, J. (2008). Cryo-Fracture or Freeze-Fracture, a Method to Expose Internal Tissue Surfaces and Cell Surfaces for Viewing in the Scanning Electron Microscope. Microscopy Today, 16(4), 56-59. doi:10.1017/S1551929500059812) and/or lyophilization (generally described in https://www.fda.gov/inspections-compliance-enforcement-and-criminal-investigations/inspection-guides/lyophilization-parenteral-793 accessed Jun. 27, 2022) while processing the placental tissues, which also leads to the loss of various endogenous growth factors during processing of these compositions when compared to human placental tissue in vivo. For example, U.S. Pat. No. 6,933,326 discloses processing human amnion and chorion via a cryofracturing process. Cryofracturing is a technique that requires the presence of water within a particular cell and/or tissue undergoing this process. During this process, the cell and/or tissue is rapidly and drastically cooled (i.e., frozen), then fractured under vacuum. The water present in the cell and/or tissue forms ice crystals due to rapid cooling and fractures the cellular membranes in the cells and/or tissues undergoing cryofracturing. It should be noted that the presence of water before freezing the cells/tissues subjected to cryofracturing increases the likelihood of various degradative processes (apoptosis, necroptosis, lysosomal degradation, etc.) within the cells/tissues, which further leads to loss of endogenous growth factors found within the human placental tissue and further leads to reduced and/or limited wound healing capabilities of these compositions. Likewise, the physical process of fracturing the cells/tissues during cryofracturing due to the presences of ice crystals increases the likelihood of degradative processes (lysosomal degradation) within the cells/tissues, which further leads to loss of endogenous growth factors found within the human placental tissue in vivo and further leads to reduced and/or limited wound healing capabilities of compositions formed with cryofracturing and/or lyophilization due to the loss of various endogenous growth factors during processing of these compositions.

SUMMARY

In view of the above, it is an object of the invention to provide micronized or sterile micronized compositions that include human amnion, human chorion, and the intermediate spongy layer that include and/or mimic growth factor profiles of the human placenta in vivo. These compositions are preferably minimally processed and further advantageously exhibit improved wound healing due to the preservation of various endogenous growth factors therein. In certain aspects, the compositions disclosed herein are micronized compositions and/or are sterile micronized compositions that are prepared from intact placental tissue (in cross section) comprising a human amnion layer, human chorion layer, and an intact human intermediate spongy layer positioned between and connecting the human amnion layer to the human chorion layer such that immediately before micronization the human amnion layer and the human chorion layer are not separated from one another thereby preserving various endogenous growth factors therein when compared to the growth factor profile of the human placenta in vivo. Moreover, the compositions disclosed herein are advantageously not subjected to harsh processing conditions such as cryofracturing and/or lyophilization during preparation of the disclosed compositions, thereby avoiding degradation of growth factors often observed with cryofracturing and/or lyophilization.

In certain aspects, disclosed herein is a micronized composition or a sterile micronized composition prepared from intact human placental tissue that is configured for wound healing, the micronized or sterile micronized composition including (a) micronized human amnion; (b) micronized human chorion; and (c) micronized human intermediate spongy layer. In certain aspects, disclosed herein is a micronized composition or a sterile micronized composition prepared from intact human placental tissue that is configured for wound healing, the micronized or sterile micronized composition consists essentially of (a) micronized human amnion; (b) micronized human chorion; and (c) micronized human intermediate spongy layer. In certain aspects, disclosed herein is a micronized composition or a sterile micronized composition prepared from intact human placental tissue that is configured for wound healing, the micronized or sterile micronized composition consists of (a) micronized human amnion; (b) micronized human chorion; and (c) micronized human intermediate spongy layer.

In certain aspects, the micronized human amnion comprises 10% to 20% of the total weight of the micronized composition or the sterile micronized composition.

In certain aspects, the micronized human chorion comprises 65% to 75% of the total weight of the micronized composition or the sterile micronized composition.

In certain aspects, the micronized human intermediate spongy layer comprises 10% to 20% of the total weight of the micronized composition or the sterile micronized composition.

In certain aspects, the micronized or sterile micronized composition comprises at least two of the following: interleukin-1 receptor antagonist (IL-1ra) ranging from $1.0 \times 10^2$ to $5.0 \times 10^4$ pg/cm$^2$; hepatocyte growth factor (HGF) ranging from $5.0 \times 10^2$ to $1.0 \times 10^4$ pg/cm$^2$; vascular endothelial growth factor receptor 1 (VEGFR1) ranging from $5.0 \times 10^2$ to $5.0 \times 10^3$ pg/cm$^2$; hyaluronic acid (HA) ranging from $1.0 \times 10^7$ to $1.0 \times 10^8$ pg/cm$^2$; glycosaminoglycans (GAGs); and Collagen.

In certain aspects, the micronized or sterile micronized composition comprises at least three of the following: IL-1ra ranging from $1.0 \times 10^2$ to $5.0 \times 10^4$ pg/cm$^2$; HGF ranging from $5.0 \times 10^2$ to $1.0 \times 10^4$ pg/cm$^2$; VEGFR1 ranging from $5.0 \times 10^2$ to $5.0 \times 10^3$ pg/cm$^2$; HA ranging from $1.0 \times 10^7$ to $1.0 \times 10^8$ pg/cm$^2$; GAGs; and Collagen.

In certain aspects, the micronized or sterile micronized composition comprises at least four of the following: IL-1ra ranging from $1.0 \times 10^2$ to $5.0 \times 10^4$ pg/cm$^2$; HGF ranging from $5.0 \times 10^2$ to $1.0 \times 10^4$ pg/cm$^2$; VEGFR1 ranging from $5.0 \times 10^2$ to $5.0 \times 10^3$ pg/cm$^2$; HA ranging from $1.0 \times 10^7$ to $1.0 \times 10^8$ pg/cm$^2$; GAGs; and Collagen.

In certain aspects, the micronized or sterile micronized composition comprises at least five of the following: IL-1ra ranging from $1.0 \times 10^2$ to $5.0 \times 10^4$ pg/cm$^2$; HGF ranging from $5.0 \times 10^2$ to $1.0 \times 10^4$ pg/cm$^2$; VEGFR 1 ranging from $5.0 \times 10^2$ to $5.0 \times 10^3$ pg/cm$^2$; HA ranging from $1.0 \times 10^7$ to $1.0 \times 10^8$ pg/cm$^2$; GAGs; and Collagen.

In certain aspects, the micronized or sterile mircronized composition comprises each of the following: IL-1ra ranging from $1.0 \times 10^2$ to $5.0 \times 10^4$ pg/cm$^2$; HGF ranging from $5.0 \times 10^2$ to $1.0 \times 10^4$ pg/cm$^2$; VEGFR1 ranging from $5.0 \times 10^2$ to $5.0 \times 10^3$ pg/cm$^2$; HA ranging from $1.0 \times 10^7$ to $1.0 \times 10^8$ pg/cm$^2$; GAGs; and Collagen.

In certain aspects, the micronized human amnion comprises diameters ranging from 1 μm to 500 μm, more preferably from 10 μm to 400 μm, and most preferably from 10 μm to 300 μm.

In certain aspects, the micronized human chorion comprises diameters ranging from 1 μm to 500 μm, more preferably from 10 μm to 400 μm, and most preferably from 10 μm to 300 μm.

In certain aspects, the micronized human intermediate spongy layer comprises diameters ranging from 1 μm to 500 μm, more preferably from 10 μm to 400 μm, and most preferably from 10 μm to 300 μm.

In certain aspects, the micronized and/or sterile micronized composition are not cryofractured.

In certain aspects, the micronized or sterile micronized composition is prepared from intact placental tissue (in cross section) comprising a human amnion layer, human chorion layer, and an intact human spongy intermediate layer positioned between and connecting the human amnion layer to the human chorion layer such that immediately before micronization the human amnion layer and the human chorion layer are not separated from one another.

In certain aspects, the micronized or sterile micronized composition is standardized to the weight of sterile, dehydrated, micronized placental tissue.

In certain aspects, the micronized or sterile micronized composition is standardized by the following equation:

$$\frac{\text{factor assayed } (pg/ml) * (\text{ml of eluate})}{\text{mg particulate}} = pg \text{ of growth facter per mg}$$

In certain aspects, the micronized or sterilize micronized composition is configured for wound packing, treatment of wounds having irregular surfaces and/or peripheral boundaries, weeping wounds, dental and/or oral wounds, or any combination thereof.

In certain aspects, also disclosed is medicament comprising the micronized or sterilize micronized composition.

In certain aspects, also disclosed is a therapeutic aerosol comprising the micronized or sterilize micronized composition configured for intranasal and/or pulmonary administration to a subject in need thereof. The therapeutic aerosol is configured to treat pulmonary disorders, trachea disorders, and a combination thereof in a subject in need thereof.

In certain aspects, also disclosed is a therapeutic bandage comprising the disclosed micronized or sterilize micronized composition configured for topical wound treatment for a subject in need thereof. The therapeutic bandage comprises a cellulose matrix, a polymeric matrix, or a combination thereof having the disclosed micronized or sterile micronized composition embedded therein. The cellulose matrix comprises a carboxyalkyl cellulose matrix or a hydroxyalkyl cellulose matrix. In certain aspects, the therapeutic bandage is configured to time release the sterile micronized composition to the wound over a predetermined time-period (e.g., 1 days to 7 days, more preferably 2 days to 3 days).

In certain aspects, the compositions disclosed herein do not use the placental disc and/or are not formed into a placental disc post-production of the micronized and/or sterile micronized compositions disclosed herein. In certain aspects, the micronized and/or sterile micronized compositions disclosed herein do not further utilize a carrier (e.g., liposomes, polymeric micelles, microspheres, nanoparticles and emulsions). In certain aspects, the amnion and chorion of the micronized and sterile micronized compositions are not separated immediately prior to micronization and do not include any recombining or re-layering of the amnion, chorion, and/or intermediate spongy layer immediately before micronization. In certain aspects, the micronized and/or sterile micronized compositions disclosed herein are not injectable compositions (e.g., subcutaneous, intravenous and/or intramuscular injectable compositions) and do not further include anesthetics (e.g., lidocaine, bupivacaine, mepivacaine, etc.).

Embodiments of the invention can include one or more or any combination of the above features and configurations. Additional features, aspects and advantages of the invention will be set forth in the detailed description that follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

Figure 1:
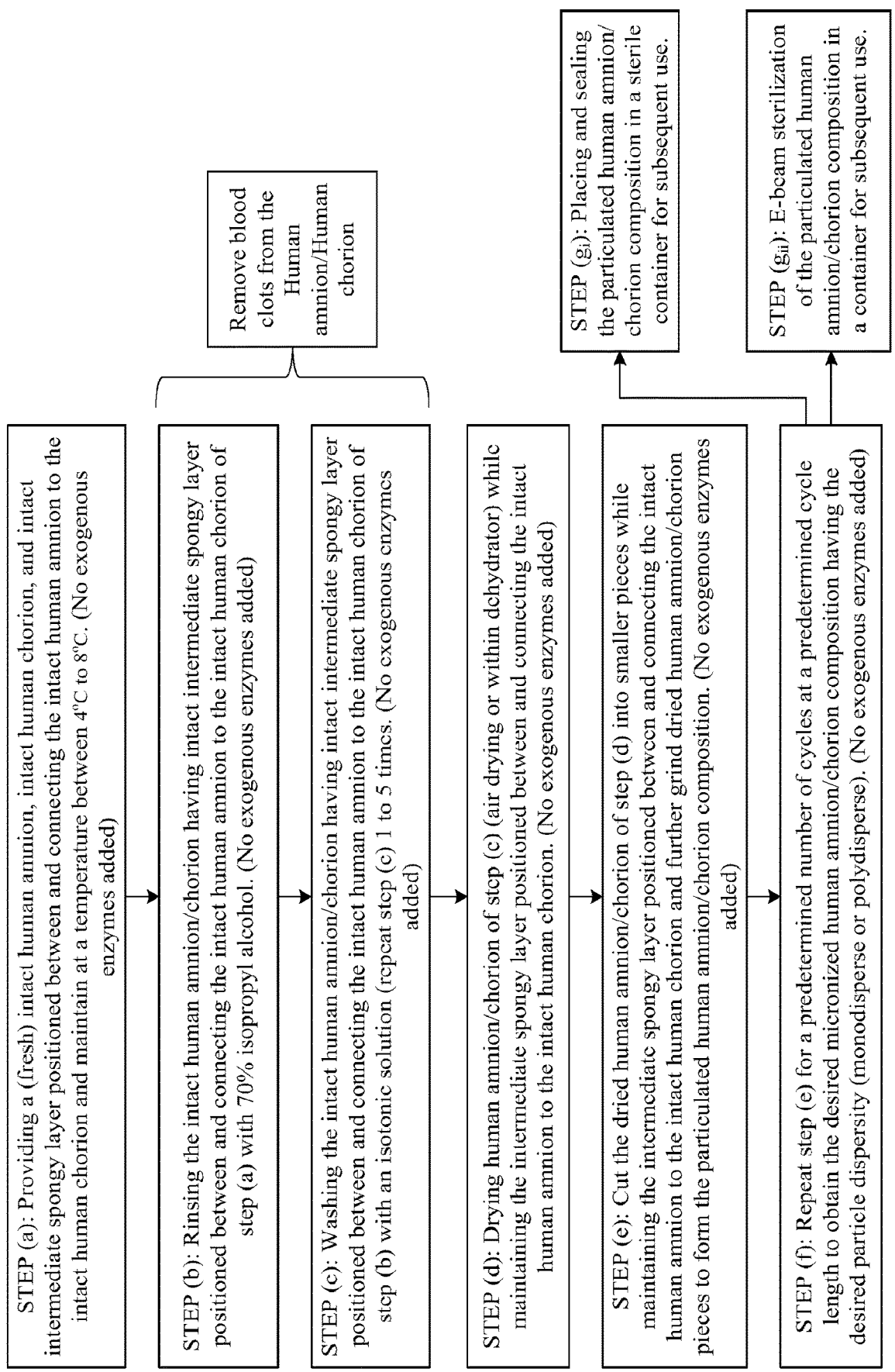
FIG. 1 is schematic depicting the steps included for preparing the micronized compositions or a sterile micronized compositions disclosed herein.

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

It must be noted that, as used in the specification and the appended claims, the singular forms "a", "an", and "the" include plural referents unless the context clearly dictates otherwise.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

"Standardization" as referred to herein allows for an accurate determination of growth factors and components within the disclosed micronized and sterile micronized compositions for subsequent use and treatment(s) (e.g., wound healing treatments) in subjects in need thereof. Applicant has determined the range of delivered factors per mg as delivered to the patient (subject in need thereof) in particulate form. What this means is that the amount of IL-1ra, HGF, VEGFR1, HA, etc. delivered to the patient/subject in need thereof is measured as the amount eluted from the particulate per mg of particulate. The quantification process used for standardization of the disclosed micronized compositions and sterile micronized compositions are used to accurately reflect the relationship between particulate (mass of particulate) and the growth factors and other chemical components therein. The standardization calculation is determined from the equation:

$$\frac{\text{factor assayed }(pg/ml) * (\text{ml of eluate})}{\text{mg particulate}} = pg \text{ of growth facter per mg}$$

This is accomplished by weighing the sample. The sample is placed in buffer for 48-72 hours, 37° C. The contents are collected and assayed for the desired components. The results are multiplied by the amount of buffer collected. This number is divided by the mg of sample used. This can be utilized for any volume of eluate used and any sample size. The testing presented in this invention utilized the particulate in a buffered solution at 37° C. for 72 hours, mimicking the application of the particulate to a wound space, internal or external. The eluate is collected and analyzed, mimicking what was eluted from the particulate to the wound. This results in a controlled and relatable amount of particulate that has been tested, yielding a controlled, relatable, and quantifiable amount of growth factors and stromal components.

Figure 2:
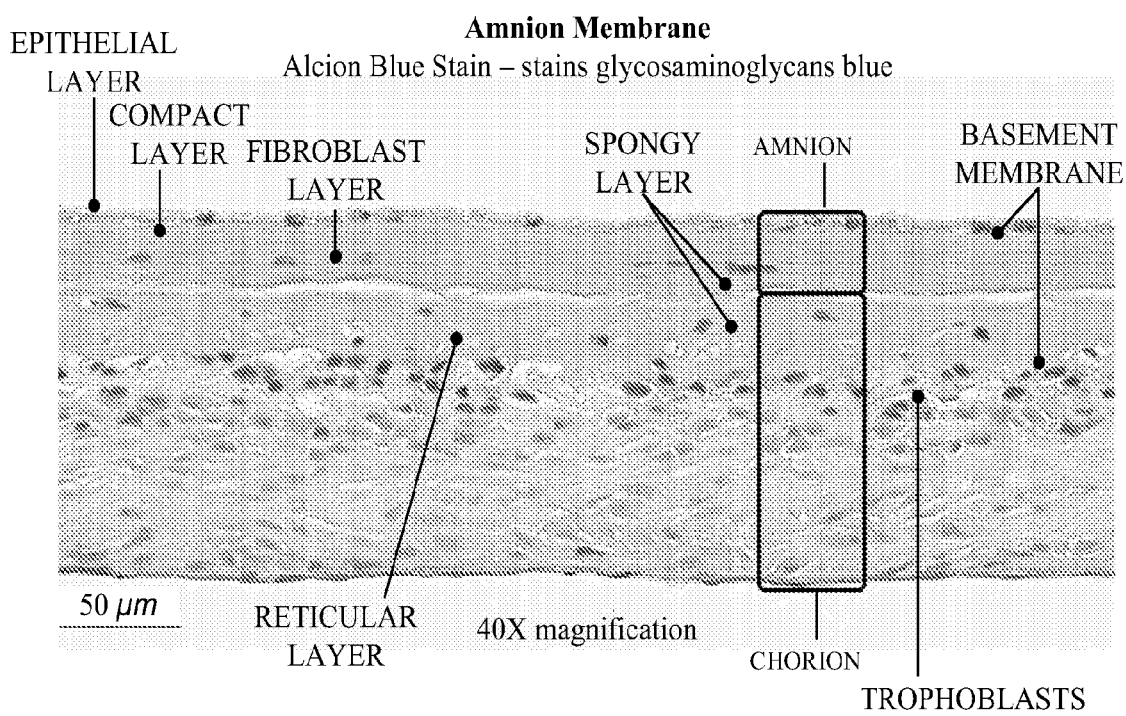
FIG. 2 is a cross-section of an exemplary human amnion and chorion membrane having an intact human spongy intermediate spongy layer positioned between and connecting the human amnion layer to the human chorion layer that is stained with Alcian Blue Stain.
Figure 3:
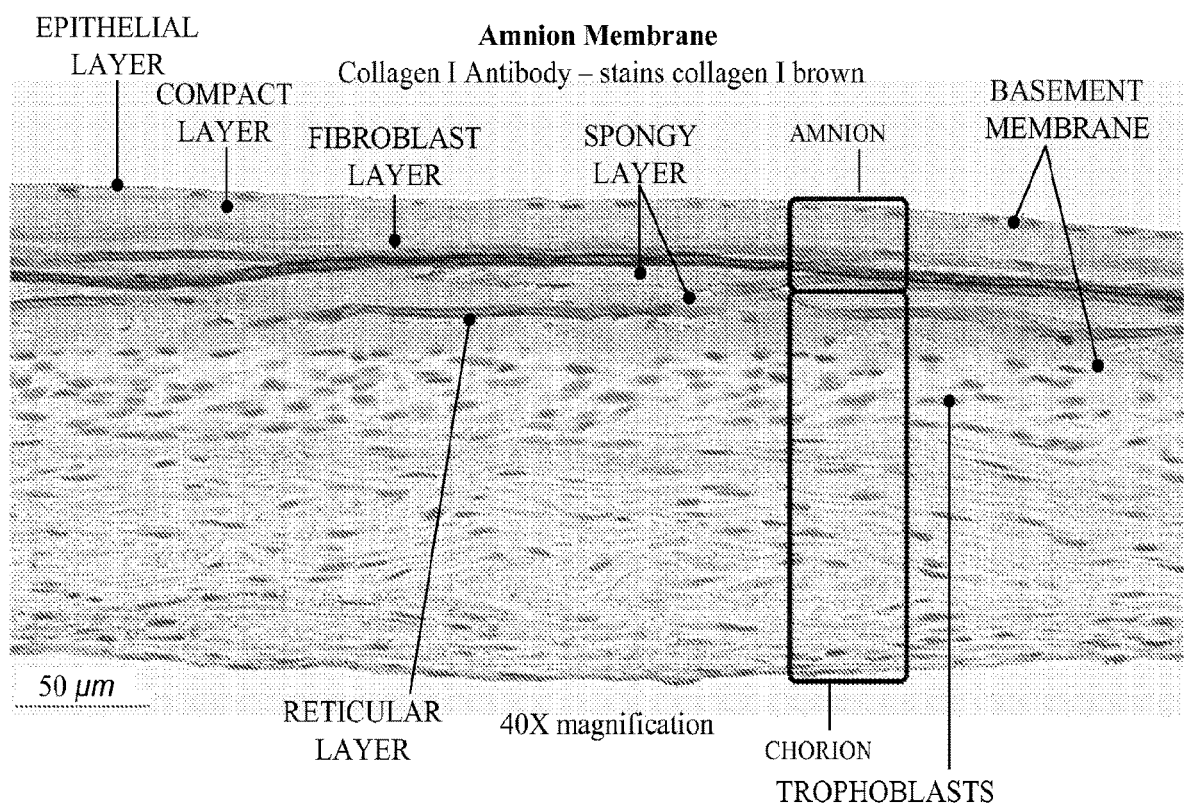
FIG. 3 is a cross-section of an exemplary human amnion and chorion membrane having an intact human spongy intermediate spongy layer positioned between and connecting the human amnion layer to the human chorion layer that is stained with a Collagen I antibody stain.
Figure 4:
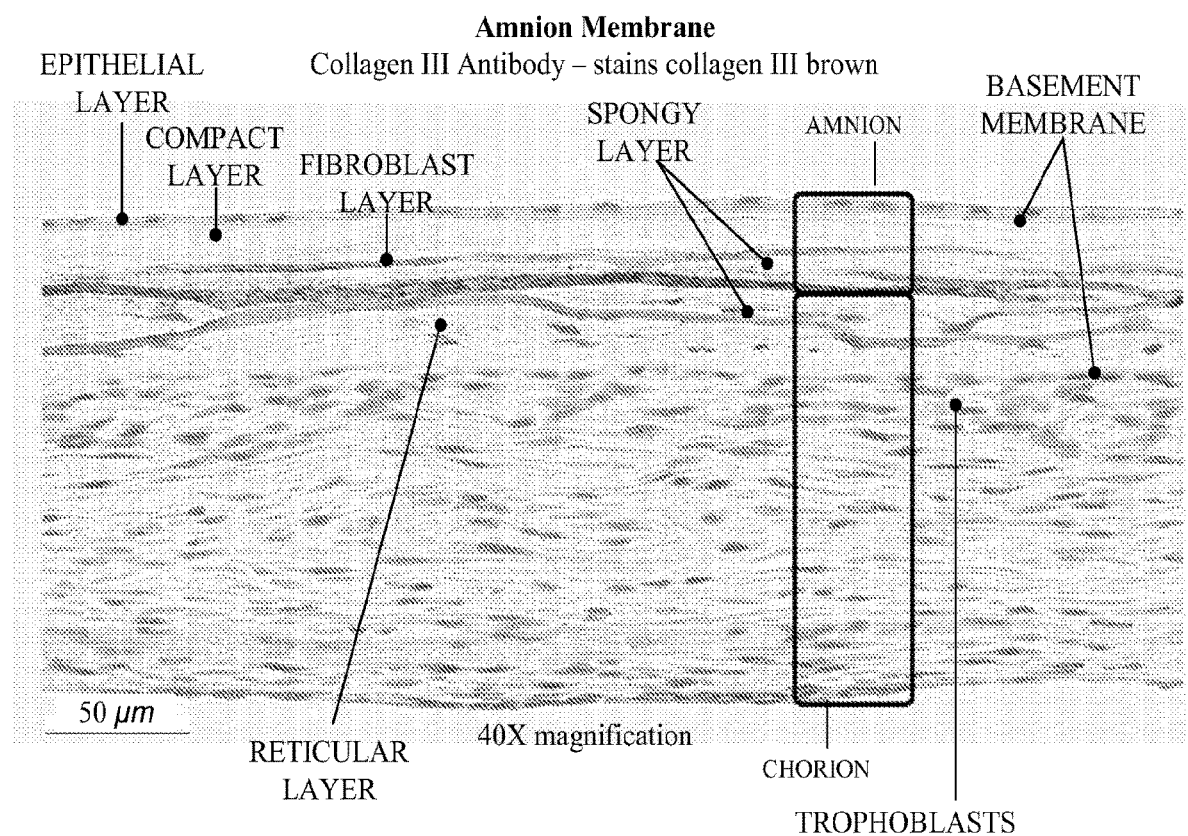
FIG. 4 is a cross-section of an exemplary human amnion and chorion membrane having an intact human spongy intermediate spongy layer positioned between and connecting the human amnion layer to the human chorion layer that is stained with a Collagen IIII antibody stain.

"Intact human placental tissue" and/or "intact placental tissue in cross-section" as defined herein and as further shown in FIGS. 2-4 includes a human amnion layer, human chorion layer, and an intact human spongy intermediate layer positioned between and connecting the human amnion layer to the human chorion layer such that immediately before micronization the human amnion layer and the human chorion layer are not separated from one another and/or the human spongy intermediate layer has not been removed.

"Cryofracturing" is a technique that requires the presence of water within a particular cell and/or tissue undergoing this process. During this process, the cell and/or tissue is rapidly and drastically cooled (i.e., frozen), then fractured under vacuum. The water present in the cell and/or tissue forms ice crystals due to rapid cooling and fractures the cellular membranes in the cells and/or tissues undergoing cryofracturing. Taylor, J. (2008). Cryo-Fracture or Freeze-Fracture, a Method to Expose Internal Tissue Surfaces and Cell Surfaces for Viewing in the Scanning Electron Microscope. *Microscopy Today*, 16(4), 56-59. doi: 10.1017/S1551929500059812

The compositions and methods described herein can comprise, consist of, or consist essentially of the essential elements and limitations described herein, as well as any additional or optional ingredients, components, or limitations described herein.

Micronized Composition Prepared from Intact Human Placental Tissue

Disclosed herein are micronized compositions (and/or sterile micronized compositions) prepared from intact human placental tissue that are used for wound healing (e.g., topical wounds including epidermal and dermal wounds/lesions, oral wounds/lesions, pulmonary and/or tracheal wounds/lesions, etc.). These compositions are minimally processed in view of human placental tissue in vivo and further advantageously exhibit improved preservation of various endogenous growth factors therein when compared with conventional compositions/formulations and further exhibit improved wound healing due to the disclosed composition's growth factor profile that mimics the growth factor profile of the human placenta (particularly the intact human amnion, human chorion, and the intermediate spongy layer positioned there between) in vivo. The micronized and sterile micronized compositions disclosed herein provide numerous advantages over currently known compositions in the field that include, but are not limited to: (1) allowing for use in and on irregular wounds as well as areas and/or wounds having fluid accumulation therein (e.g., weeping wounds); (2) standardization of growth factors in the compositions allowing for accurate determination of the concentrations of growth factors being administered to a subject in need thereof via the micronized and/or sterile micronized compositions while in use, (3) preservation of the intermediate spongy layer (and/or of the endogenous growth factors found within the intermediate spongy layer) of the human amnion and human chorion layers, and (4) quantifiable and/or controlled release of IL-1ra, HGF, VEGFR1, HA, glycosaminoglycans and collagen from the micronized compositions and/or sterile micronized compositions to recipient tissues.

In certain aspects, the compositions disclosed herein are micronized compositions and/or are sterile micronized compositions that are prepared from intact placental tissue (i.e., intact in cross section as shown, for example, in FIGS. 2-4) that include a human amnion layer, human chorion layer, and an intact human intermediate spongy layer positioned between and connecting the human amnion layer to the human chorion layer such that immediately before micronization the human amnion layer and the human chorion layer are not separated from one another thereby preserving various endogenous growth factors therein when compared to the human placenta in vivo. Moreover, the compositions disclosed herein are advantageously not subjected to harsh processing conditions such as cryofracturing and/or lyophilization, and during preparation of the disclosed compositions, the human amnion is not physically separated from the human chorion before micronization thereby preserving the intermediate spongy layer and the growth factors included therein.

In certain aspects, disclosed herein is a micronized composition or a sterile micronized composition prepared from intact human placental tissue that is configured for wound healing, the micronized or sterile micronized composition including (a) micronized human amnion; (b) micronized human chorion; and (c) micronized human intermediate spongy layer. Within the micronized composition or the sterile micronized composition, the micronized human amnion comprises 10% to 20% of the total weight of the micronized composition or the sterile micronized composition, and more preferably 10% to 18% of the total weight of the micronized composition or the sterile micronized composition. Amnion includes few growth factors in greater concentration than chorion. These include SDF-1, TGF-b1 and GAL-7 [McQuilling J P, Vines J B, Kimmerling K A, Mowry K C. Proteomic Comparison of Amnion and Chorion and Evaluation of the Effects of Processing on Placental Membranes. Wounds: a compendium of clinical research and practice. 2017; 29(6):E36-e40. Epub 2017 Jul. 7. PubMed PMID: 28682294; PMCID: PMC8009308]. Within the micronized composition or the sterile micronized composition, the micronized human chorion comprises 65% to 75% of the total weight of the micronized composition or the sterile micronized composition, and more preferably 67% to 73% of the total weight of the micronized composition or the sterile micronized composition. Chorion contains a higher concentration of most growth factors than amnion, likely due to the comparative thickness. For example, chorion has significantly more bFGF, HGF, PDGF-BB [McQuilling J P, Vines J B, Kimmerling K A, Mowry K C. Proteomic Comparison of Amnion and Chorion and Evaluation of the Effects of Processing on Placental Membranes. Wounds: a compendium of clinical research and practice. 2017; 29(6): E36-e40. Epub 2017 Jul. 2007. PubMed PMID: 28682294; PMCID: PMC8009308]. In certain aspects, the micronized human intermediate spongy layer comprises 10% to 20% of the total weight of the micronized composition or the sterile micronized composition, and more preferably 12% to 18% of the total weight of the micronized composition or the sterile micronized composition. In certain aspects and when compared with the micronized human amnion and micronized human chorion, the micronized human intermediate spongy layer is particularly rich in collagens type I, III, IV and proteoglycans, all of which are beneficial in the wound healing process. Collagen is the most abundant protein in the human body and a key component of the extracellular matrix. In wound healing, collagen attracts fibroblasts and facilitates deposition of new collagen as well as bind and inactivate excessive matrix metalloproteinase (degradation). Proteoglycans are core proteins with covalently attached glycosaminoglycan chains. They are a major component of the ECM where they complex with HA, collagen and other matrix proteins. Proteoglycans bind water, potassium, sodium, and calcium, as well as affect movement, stability, and signaling of substances within the ECM. In certain aspects, the micronized human amnion and micronized human intermediate spongy layer may be present in the micronized compositions (and/or sterile micronized compositions) at a ratio of micronized human amnion:micronized human intermediate spongy layer ranging from 2:1 to 1:2, 1.7:1 to 1:1.5, or 1:1. In certain aspects, the micronized human amnion and micronized human chorion may be present in the micronized compositions (and/or sterile micronized compositions) at a ratio of micronized human amnion:micronized human chorion ranging from 1:7.5 to 1:3.25 and/or any ratios occurring within these ranges. In certain aspects, the micronized human intermediate spongy layer and micronized human chorion may be present in the micronized compositions (and/or sterile micronized compositions) at a ratio of micronized human amnion:micronized human chorion ranging from 1:7.5 to 1:3.25 and/or any ratios occurring within these ranges.

Figure 5:
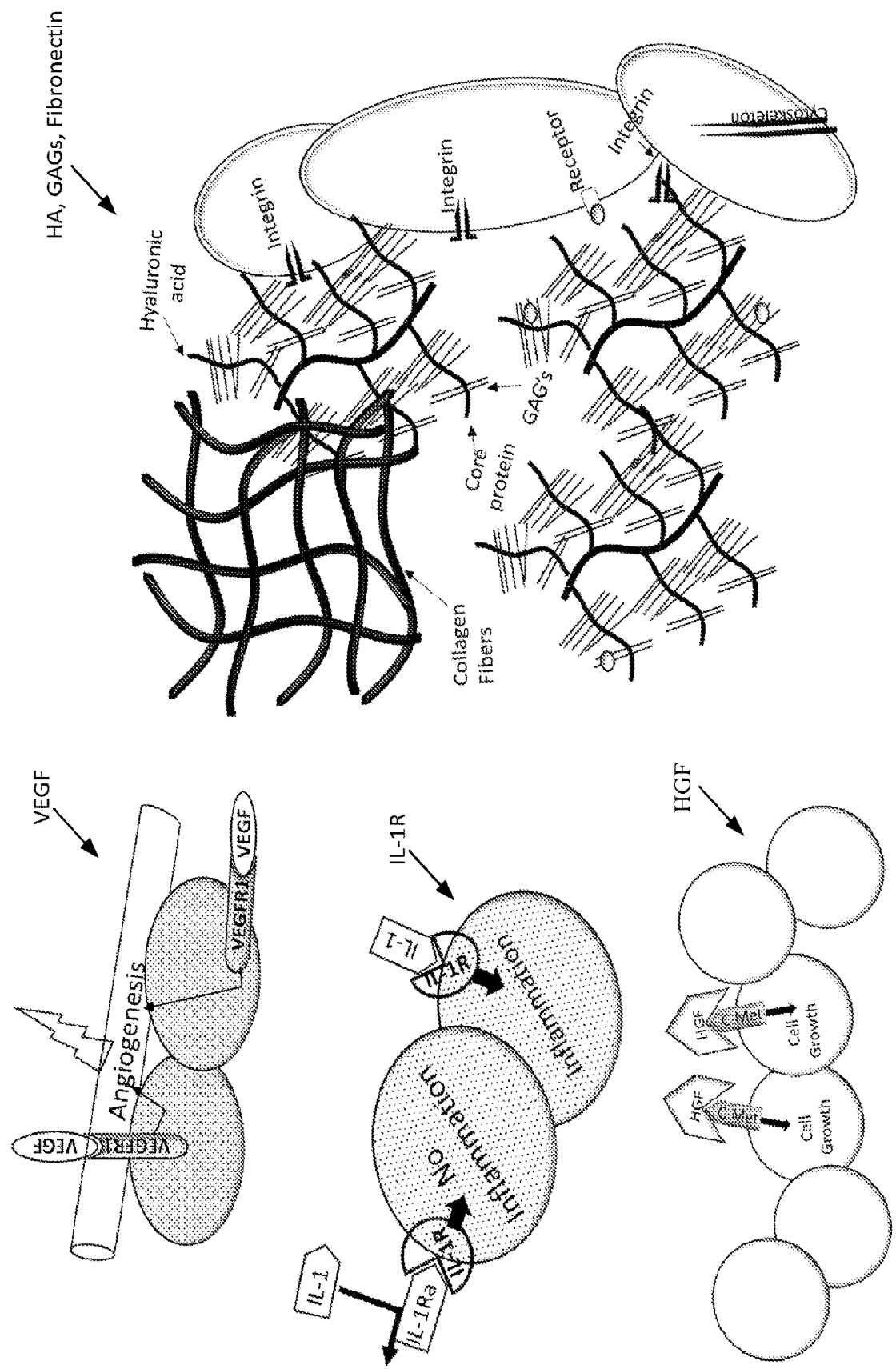
FIG. 5. depicts various human endogenous pathways activated by vascular endothelial growth factor receptor 1 (VEGFR1), interleukin-1 receptor antagonist (IL-1ra), hepatocyte growth factor (HGF), hyaluronic acid (HA), and glycosaminoglycans (GAGs) that are associated with cellular remodeling and wound healing.

The disclosed micronized compositions (and/or sterile micronized compositions) prepared from intact human placental tissues particularly include effective amounts of interleukin-1 receptor antagonist (IL-1ra), hepatocyte growth factor (HGF), vascular endothelial growth factor receptor 1 (VEGFR1), hyaluronic acid (HA), glycosaminoglycans (GAGs), and Collagen to facilitate wound healing and wound healing responses in a subject in need thereof. FIG. 5 provides general schematics demonstrating IL-1ra, HGF, VEGR1, HA, and GAGs endogenous modes of action and various signaling cascades involving these growth factors in humans in vivo. In particular, IL-1ra binds non-productively to the IL-1 (pro-inflammatory cytokine) receptor, preventing IL-1 (inflammatory molecule) from sending a signal. This results in modulation of a variety of IL-1 related immune and inflammatory responses. HGF is cellular growth, motility and morphogenic factor secreted by mesenchymal cells. It has been shown to have a major role in embryonic organ development, specifically in myogenesis, in adult organ regeneration, and in wound healing. Importantly, increased expression of HGF has been associated with the enhanced and scarless wound healing capabilities of fibroblast cells isolated from the oral mucosa tissue. VEGFR1 acts as a cell-surface receptor for VEGF-A, VEGF-B and PGF for the development of embryonic vasculature, the regulation of angiogenesis, cell survival and cell migration. VEGFR1 can promote endothelial cell proliferation, survival and angiogenesis in adulthood. Its function in promoting cell proliferation seems to be cell-type specific. For example, it promotes PGF-mediated proliferation of endothelial cells, but does not promote proliferation of normal fibroblasts (in vitro). Glycosaminoglycans (GAGs) are present in all mammalian tissues where they interact with other ECM components to organize and form structural scaffolding suitable for remodeling. GAGs also modulate cell growth and proliferation, cell adhesion, anticoagulation, and wound repair. Hyaluronic acid (HA) is a well-documented chief component of the extracellular matrix. HA is a non-sulfated glycosaminoglycan that, among other things, provides a backbone for sulfated glycosaminoglycans. HA also binds integrins resulting in stabilized ECM and absorbs water which is another chief component of the ECM. The high molecular mass of HA results in unique biophysical properties, such as, high viscoelasticity and high colloid osmotic pressure. Additionally, HA leads to extracellular matrix stabilization, water maintenance and regulation of protein distribution. Collagen is the most abundant protein in the body and a key component of the extracellular matrix, and during wound healing, collagen attract fibroblasts and encourage deposition of new collagen as well as bind and inactivate excessive matrix metalloproteinase (degradation).

In certain aspects, the micronized or sterile micronized composition includes at least one of interleukin-1 receptor antagonist (IL-1ra), hepatocyte growth factor (HGF), vascular endothelial growth factor receptor 1 (VEGFR1), hyaluronic acid (HA), glycosaminoglycans (GAGs), and Collagen in an effective amount to facilitate wound healing and wound healing responses in a subject in need thereof. In certain aspects, the micronized or sterile micronized composition includes at least two of IL-1ra, HGF, VEGFR1, HA, GAGs, and collagen in effective amounts to facilitate wound healing and wound healing responses in a subject in need thereof. In certain aspects, the micronized or sterile micronized composition includes at least three of IL-1ra, HGF, VEGFR1, HA, GAGs, and Collagen in effective amounts to facilitate wound healing and wound healing responses in a subject in need thereof. In certain aspects, the micronized or sterile micronized composition includes at least four of IL-1ra, HGF, VEGFR1, HA, GAGs, and Collagen in effective amounts to facilitate wound healing and wound healing responses in a subject in need thereof. In certain aspects, the micronized or sterile micronized composition includes at least five of IL-1ra, HGF, VEGFR1, HA, GAGs, and Collagen in effective amounts to facilitate wound healing and wound healing responses in a subject in need thereof. In certain aspects, the micronized or sterile micronized composition includes each of IL-1ra, HGF, VEGFR1, HA, GAGs, and collagen in effective amounts to facilitate wound healing and wound healing responses in a subject in need thereof.

In certain aspects, the micronized or sterile micronized composition comprises at least one of the following: interleukin-1 receptor antagonist (IL-1ra) ranging from $1.0 \times 10^2$ to $5.0 \times 10^4$ pg/cm$^2$ and more preferably ranging from ranging from $1.0 \times 10^2$ to $6.0 \times 10^3$ pg/cm$^2$; hepatocyte growth factor (HGF) ranging from $5.0 \times 10^2$ to $1.0 \times 10^4$ pg/cm$^2$ and more preferably ranging from $6.0\times10^2$ to $7.5\times10^3$ pg/cm$^2$; vascular endothelial growth factor receptor 1 (VEGFR1) ranging from $5.0\times10^2$ to $5.0\times10^3$ pg/cm$^2$ and more preferably ranging from $8.0\times10^2$ to $3.0\times10^3$ pg/cm$^2$ hyaluronic acid (HA) ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and Collagen to facilitate wound healing and wound healing responses in a subject in need thereof. In certain aspects, the micronized or sterile micronized composition comprises at least two of the following: IL-1ra ranging from $1.0\times10^2$ to $5.0\times10^4$ pg/cm$^2$ and more preferably ranging from ranging from $1.0\times10^2$ to $6.0\times10^3$ pg/cm$^2$; HGF ranging from from $5.0\times10^2$ to $1.0\times10^4$ pg/cm$^2$ and more preferably ranging from $6.0\times10^2$ to $7.5\times10^3$ pg/cm$^2$; VEGFR1 ranging from $5.0\times10^2$ to $5.0\times10^3$ pg/cm$^2$ and more preferably ranging from $8.0\times10^2$ to $3.0\times10^3$ pg/cm$^2$; HA ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and collagen to facilitate wound healing and wound healing responses in a subject in need thereof. In certain aspects, the micronized or sterile micronized composition comprises at least three of the following: IL-1ra ranging from $1.0\times10^2$ to $5.0\times10^4$ pg/cm$^2$ and more preferably ranging from ranging from $1.0\times10^2$ to $6.0\times10^3$ pg/cm$^2$; HGF ranging from from $5.0\times10^2$ to $1.0\times10^4$ pg/cm$^2$ and more preferably ranging from $6.0\times10^2$ to $7.5\times10^3$ pg/cm$^2$; VEGFR1 ranging from $5.0\times10^2$ to $5.0\times10^3$ pg/cm$^2$ and more preferably ranging from $8.0\times10^2$ to $3.0\times10^3$ pg/cm$^2$; HA ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and collagen to facilitate wound healing and wound healing responses in a subject in need thereof. In certain aspects, the micronized or sterile micronized composition comprises at least four of the following: IL-1ra ranging from $1.0\times10^2$ to $5.0\times10^4$ pg/cm$^2$ and more preferably ranging from ranging from $1.0\times10^2$ to $6.0\times10^3$ pg/cm$^2$; HGF ranging from from $5.0\times10^2$ to $1.0\times10^4$ pg/cm$^2$ and more preferably ranging from $6.0\times10^2$ to $7.5\times10^3$ pg/cm$^2$; VEGFR1 ranging from $5.0\times10^2$ to $5.0\times10^3$ pg/cm$^2$ and more preferably ranging from $8.0\times10^2$ to $3.0\times10^3$ pg/cm$^2$; HA ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and collagen to facilitate wound healing and wound healing responses in a subject in need thereof. In certain aspects, the micronized or sterile micronized composition comprises at least five of the following: IL-1ra ranging from $1.0\times10^2$ to $5.0\times10^4$ pg/cm$^2$ and more preferably ranging from ranging from $1.0\times10^2$ to $6.0\times10^3$ pg/cm$^2$; HGF ranging from $5.0\times10^2$ to $1.0\times10^4$ pg/cm$^2$ and more preferably ranging from $6.0\times10^2$ to $7.5\times10^3$ pg/cm$^2$; VEGFR1 ranging from $5.0\times10^2$ to $5.0\times10^3$ pg/cm$^2$ and more preferably ranging from $8.0\times10^2$ to $3.0\times10^3$ pg/cm$^2$; HA ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and collagen to facilitate wound healing and wound healing responses in a subject in need thereof. In certain aspects, the micronized or sterile mircronized composition comprises each of the following: IL-1ra ranging from $1.0\times10^2$ to $5.0\times10^4$ pg/cm$^2$ and more preferably ranging from ranging from $1.0\times10^2$ to $6.0\times10^3$ pg/cm$^2$; HGF ranging from from $5.0\times10^2$ to $1.0\times10^4$ pg/cm$^2$ and more preferably ranging from $6.0\times10^2$ to $7.5\times10^3$ pg/cm$^2$; VEGFR1 ranging from $5.0\times10^2$ to $5.0\times10^3$ pg/cm$^2$ and more preferably ranging from $8.0\times10^2$ to $3.0\times10^3$ pg/cm$^2$; HA ranging from $1.0\times10^7$ to $1.0\times10^8$ pg/cm$^2$ and more preferably from $1.5\times10^7$ to $9.5\times10^7$ pg/cm$^2$; glycosaminoglycans (GAGs); and collagen to facilitate wound healing and wound healing responses in a subject in need thereof. Any endpoint falling within the above disclosed ranges serve as the basis for additional sub-ranges falling therein.

In certain aspects, the micronized human amnion comprises diameters ranging from 1 μm to 500 μm, preferably from 10 μm to 300 μm. The micronized human chorion comprises diameters ranging from 1 μm to 500 μm, preferably from 10 μm to 300 μm. The micronized human intermediate spongy layer comprises diameters ranging from 1 μm to 500 μm, preferably from 10 μm to 300 μm. It should be appreciated that because the human amnion, human chorion, and human intermediate spongy layer are not separated from one another prior to micronization that the micronized particles included within the disclosed compositions may each contain any combination of micronized human amnion, micronized human chorion, and/or the human intermediate spongy layer. For example, it is contemplated that the particles disclosed herein may include (1) human amnion alone, (2) human chorion alone, (3) human intermediate spongy layer, (4) a combination human amnion, human chorion, and human intermediate spongy layer, (5) a combination of human amnion and human intermediate spongy layer, or (6) a combination human chorion and human intermediate spongy layer.

To better achieve consistent therapeutic wound healing effects and uniform deliverable growth factor concentrations to a subject in need thereof, the micronized or sterile micronized composition is standardized to the weight of micronized placental tissue. The micronized or sterile micronized composition is standardized by the following:

$$\frac{\text{factor assayed } (pg/\text{ml}) * (\text{ml of eluate})}{\text{mg particulate}} = pg \text{ of growth facter per mg}$$

As alluded to above, the disclosed micronized or sterilize micronized composition has various wound healing applications and is particularly configured for wound packing, treatment of wounds having irregular surfaces and/or peripheral boundaries (e.g., wounds to the epidermis and/or dermis), weeping wounds, dental and/or oral wounds, or any combination thereof. The particle diameter, size, and consistency of the disclosed micronized compositions and sterile micronized compositions allow for direct application to the above-mentioned wounds having irregular surfaces and/or peripheral boundaries as well as the above-mentioned weeping wounds. In particular and unlike conventional human amnion laminates and/or human chorion laminate (which have planar outer surfaces), the size and shape of the disclosed micronized compositions and sterile micronized compositions facilitate adherence to the above-mentioned wounds and subsequent release of the above-mentioned.

The micronized or sterilize micronized compositions disclosed herein may be further configured as a therapeutic aerosol configured for intranasal and/or pulmonary administration to a subject in need thereof. In this aspect, the micronized or sterilize micronized compositions disclosed herein may be included within, for example, an inhaler and/or nasal delivery device and may further include an inert propellant to aid in pulmonary and/or nasal delivery of the micronized or sterile micronized compositions to a subject in need thereof. The therapeutic aerosol is configured to treat pulmonary wounds, pulmonary lesions, and/or pulmonary disorders, trachea wounds, trachea lesions, and/or trachea disorders, and a combination thereof in a subject in need thereof.

In certain aspects, also disclosed are therapeutic bandages comprising micronized or sterile micronized composition configured for topical wound treatment (e.g., of wounds to the epidermis and dermis) to a subject in need thereof. The therapeutic bandage comprises a cellulose matrix, a polymeric matrix, or a combination thereof having the disclosed micronized and/or sterile micronized compositions embedded therein. The cellulose matrix comprises a carboxyalkyl cellulose matrix or a hydroxyalkyl cellulose matrix. In certain aspects, the therapeutic bandage is configured to time release the sterile micronized composition to the wound over a predetermined time-period. In an aspect, the present invention relates to a micronized or sterile micronized composition for use in the treatment of a wound in a human subject in need thereof, the treatment comprising contacting the wound with micronized or sterile micronized composition for a predetermined time period to facilitate wound healing in the human subject in need thereof. The sterile human placental allograft for use, wherein the micronized or sterile micronized composition is implanted in or applied on a wound in the subject in need thereof. The micronized or sterile micronized composition for use, wherein the wound is an internal wound within the subject in need thereof and/or a dental wound. The micronized or sterile micronized composition for use, wherein the micronized or sterile micronized composition is topically applied to the wound in the human subject in need thereof. The micronized or sterile micronized composition for use, wherein the wound is a diabetic ulcer. The micronized or sterile micronized composition for use, wherein the wound is a diabetic foot ulcer.

Method of Making the Micronized Composition Prepared from Intact Human Placental Tissue FIG. 1 generally discloses the method of making the micronized compositions (and sterile micronized compositions) disclosed herein from intact human placental tissue (i.e., human amnion, human chorion, and the intermediate spongy layer positioned between and connecting the human chorion to the human amnion). The method disclosed herein does not utilize any exogenous enzymes during the method of making the disclosed compositions nor are any exogenous enzymes added to the disclosed micronized compositions (and sterile micronized compositions) to ensure that the growth factor profile of the disclosed compositions mimic the growth factor profile of human amnion, human chorion, and the intermediate spongy layer positioned between the human chorion and human amnion in vivo resulting in improved wound healing efficacy of compositions produced therefrom. Moreover, unlike conventional processes in the field, lyophilization processes and/or cryofacturing processes are not utilized while making the disclosed compositions because lyophilization (or freeze-drying) and/or cryofracturing (or freeze fracture) can lead to degradation of various growth factors in the compositions produced therefrom and ultimately lead to diminished wound healing efficacy of compositions produced therefrom.

As specifically shown in FIG. 1, step (a), fresh, intact placental tissue is provided from a human donor within 24 to 96 hours post-extraction from the donor and more preferably from 24 to 72 hours post-extraction from the donor. This fresh, intact placental tissue includes an intact human amnion, intact human chorion, and intact intermediate spongy layer positioned between and connecting the intact human amnion to the intact human chorion. Before and during step (a), the fresh, intact placental tissue is maintained at a temperature between 4° C. to 8° C. to reduce and/or minimize degradation of the placental tissue (e.g., via apoptosis, necroptosis, and/or lysosomal degradation). Moreover, throughout the method disclosed immediately below and further depicted in FIG. 1, the temperature is preferably maintained between 4° C. to 20° C. and more preferably from 4° C. to 8° C. to reduce and/or minimize degradation of the placental tissue and the compositions resulting from this method.

After step (a), step (b) occurs in which the intact human amnion/chorion having intact intermediate spongy layer positioned between and connecting the intact human amnion to the intact human chorion of step (a) is rinsed/with an alcohol solution to rinse away any extraneous non-amnion human placental components and/or any other potential contaminants for a predetermined time period, in which the predetermined time period ranges from 60 seconds to 120 seconds and in preferred aspects is 90 seconds. In certain aspects, the alcohol solution preferably is isopropyl alcohol at a concentration of 70% to 100%. In preferred embodiments the alcohol concentration ranges from 70% to 75%, and in most preferred embodiments, the alcohol is 70% isopropyl alcohol. Isopropyl alcohol is preferred over other commercially available lab and/or pharmaceutical grade alcohols, such as ethanol, because isopropyl alcohol advantageously disinfects and cleans the human amnion without damaging (e.g., unduly dehydrating, initiating apoptotic processes, and/or necrotic processes) the placental tissue.

After step (b), step (c) occurs in which the intact human amnion/chorion having intact intermediate spongy layer positioned between and connecting the intact human amnion to the intact human chorion of step (b) is washed with an isotonic solution to rinse away any extraneous non-amnion human placental components and/or any other potential contaminants. The isotonic solution includes, for example, phosphate buffered saline (PBS) (1×PBS), (or alternatively one of lactated ringers (NaCL 6 g/L, Sodium Lactate 3.1 g/L, KCl 0.3 g/L, and CaCl 0.2 g/L at pH 6.5), isotonic saline (0.9 wt % NaCl), Plasma-Lyte® (NaCl 5.26 g/L, KCl 0.37 g/L, Magnesium Chloride hexahydrate 0.30 g/L, Sodium Acetate trihydrate 3.68 g/L, Sodium Gluconate 5.02 g/L at pH 7.4), Normosol® (NaCl 5.26 g/L, KCl 0.37 g/L, Magnesium Chloride 0.30 g/L, Sodium Acetate anhydrous 2.22 g/L, Sodium Gluconate 5.02 g/L at pH 7.4)). The washing step of step (c) may occur once and/or may be repeated one time, two times, three times, or four times with each wash step occurring for 5 to 15 minutes with a predetermined volume (e.g., 300 mL to 1000 mL, preferably 500 mL) of the isotonic solution at a temperature ranging from 4° C. to 20° C. and more preferably 4 to 15° C. for a time-period of from 5 minutes to 15 minutes.

In certain aspects, before step (b), during step (b), before step (c), and/or during step (c) one should further determine whether any blood clots and/or blood pool(s) are present in the placental tissue (i.e., the amnion, chorion, and spongy intermediate layer), and if present, the blood clots/blood pools are removed from the intact human amnion/chorion having intact intermediate spongy layer positioned between and connecting the intact human amnion to the intact human chorion. If present, the blood clots are removed via suction or other mechanical removal means (e.g., scalpel, forceps and gauze) to further ensure that the presence of any immunogenic components (e.g., hemoglobin and/or heme associated components from the human amnion donor) are minimized in the end resulting micronized composition and/or sterile micronized composition thereby avoiding and/or minimizing an immunogenic response by the subject when the disclosed compositions are administered to a subject in need thereof.

During steps (b) and (c) as well as throughout the entire method (i.e., all steps) depicted in FIG. 1, it is imperative to maintain an aseptic and/or sterile work environment to prevent and/or reduce introduction of any contaminants while making micronized composition (and/or sterile micronized composition).

After step (c), a drying step (d) occurs in which the intact human amnion/chorion having intact intermediate spongy layer positioned between and connecting the intact human amnion to the intact human chorion of step (c) is then subjected to drying during step (d) thereby forming dried intact human amnion/chorion having intact intermediate spongy layer positioned between and connecting the intact human amnion to the intact human chorion. In particular, during step (d), the amnion/chorion is laid flat and set at ambient temperature for 2-6 hours in the biosafety cabinet with circulating fan, or in a dehydrator for 1 hour to 24 hours, more preferably from 4 hours to 24 hours (at a temperature ranging 30° C. to 40° C.). The end resulting dried intact human amnion/chorion having intact intermediate spongy layer positioned between and connecting the intact human amnion to the intact human chorion has a maximum water content ranging from 10 wt % to 15 wt %, which renders the dried intact human amnion/chorion having intact intermediate spongy layer positioned between and connecting the intact human amnion to the intact human chorion unsatisfactory to undergo any know cryofracturing processes in the art and which further reduces the likelihood of any endogenous degradative processes reliant on the presence of water thereby further minimizing growth factor degradation during the method of FIG. 1.

After step (d), the dried intact human amnion/chorion having intact intermediate spongy layer positioned between and connecting the intact human amnion to the intact human chorion is further re-sized into smaller portions in order to undergo subsequent grinding/particulation processes. It should be noted that during the re-sizing of step (d), the human amnion, human chorion, and intermediate spongy layer are not separated from one another. Instead, the cross-section portions of the human placental tissue, shown for example in FIGS. 2-4, remain intact (especially in cross-section) such that the human chorion and human amnion remain connected to one another by an intact spongy intermediate layer position there between.

During step (e), the re-sized dried intact human amnion/chorion having intact intermediate spongy layer positioned between and connecting the intact human amnion to the intact human chorion is further subjected to a grinding process to form the micronized or sterile micronized compositions prepared from intact human placental tissue that are configured for wound healing as disclosed herein. In particular, during step (e), the re-sized dried intact human amnion/chorion having intact intermediate spongy layer positioned between and connecting the intact human amnion to the intact human chorion is subjected to a milling and/or cryomilling process (grinding process) configured to yield particles (polydisperse or monodisperse particles) having sizes ranging from greater than 1 µm to 500 µm, greater than 1 µm to 400 µm, greater than 1 µm to 300 µm, greater than 1 µm to 200 µm, greater than 1 µm to 100 µm, greater than 1 µm to 50 µm, than 1 µm to 25 µm, greater than 50 µm to 500 µm, greater than 50 µm to 400 µm, greater than 50 µm to 300 µm, greater than 50 µm to 200 µm, greater than 50 µm to 100 µm, greater than 10 µm to 500 µm, greater than 10 µm to 400 µm, greater than 10 µm to 300 µm, greater than 10 µm to 200 µm, greater than 10 µm to 100 µm wherein any endpoint falling within these ranges may serve as endpoints for additional ranges. Due to the above mentioned processing conditions, the particles may include various combinations of the human amnion, human chorion, and spongy intermediate layer that include the following: (1) particles having human amnion alone, (2) particles having human chorion alone, (3) particles having human intermediate spongy layer, (4) particles having a combination human amnion, human chorion, and human intermediate spongy layer, (5) particles having a combination of human amnion and human intermediate spongy layer, or (6) particles having a combination human chorion and human intermediate spongy layer.

In certain aspects, the grinding during step (e) is a cryomilling process (as described, for example, US 20160287749, US 20170203004, and U.S. Pat. No. 10,105, 398, which are each incorporated by reference in their entirety herein) in which the re-sized dried intact human amnion/chorion having intact intermediate spongy layer positioned between and connecting the intact human amnion to the intact human chorion step (e) is placed into a liquid nitrogen cooled cryomill chamber and subjected to grinding therein thereby forming the micronized and sterile micronized compositions prepared from intact human placental tissue that are configured for wound healing and having the above mentioned particle diameter(s).

In certain aspects, each grinding and/or milling (cryomilling) cycle is for a duration of 30 seconds to 4 minutes, of 30 seconds to 3 minutes, of 1.0 to 2.5 minutes. As further shown in FIG. 1, the method for producing the micronized or sterile micronized compositions disclosed herein may further include step (f), which is repeating the grinding and/or milling process of step (e) for an additional number of predetermined cycles (e.g., 1 additional cycle, 2 additional cycles, 3 additional cycles, 4 additional cycles, 5 additional cycles, 6 additional cycles, etc.) in which each additional cycle has a predetermined time duration (e.g., 30 seconds to 4 minutes, of 30 seconds to 3 minutes, of 1.0 to 2.5 minutes). These additional cycles result in a smaller and more homogeneous particle diameter of the micronized and sterile micronized compositions.

During step ($g_i$), the micronized and sterile micronized compositions of step (e) and/or step (f) are placed and sealed in a sterile container and are stored at predetermined temperatures for subsequent use in a subject in need thereof for the various therapeutic purposes disclosed herein. or, during step ($g_{ii}$), the micronized and sterile micronized compositions of step (e) and/or step (f) are placed and sealed in a container and are E-beam sterilized for subsequent use in a subject in need thereof for the various therapeutic purposes disclosed herein.

As discussed above and while preparing the micronized and sterile micronized compositions disclosed herein, the human amnion, human chorion, and intermediate spongy layer are not separated from one another. The above mentioned steps ensures, unlike other compositions in the field that remove the intermediate spongy layer and lose portions of the intermediate spongy layer by physically separating the amnion from the chorion, that substantially all of the intermediate spongy layer remains in the micronized and sterile micronized compositions disclosed herein. The intermediate spongy layer includes collagens type I, III, IV as well as proteoglycans, all of which are beneficial in the wound healing process. Collagen is the most abundant protein in the human body and a key component of the extracellular matrix. In wound healing, collagen attracts fibroblasts and facilitates deposition of new collagen as well as bind and inactivate excessive matrix metalloproteinase (degradation).

Proteoglycans are core proteins with covalently attached glycosaminoglycan chains. They are a major component of the ECM where they complex with HA, collagen and other matrix proteins. They affect the movement, stability and signaling of substances within the ECM, along with binding water, sodium, potassium and calcium.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

WORKING EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature if not listed, and pressure is at or near atmospheric. There are numerous variations and combinations of conditions, e.g., component concentrations, temperatures, pressures and other reaction ranges and conditions that can be used to optimize the product purity and yield obtained from the described process. Only reasonable and routine experimentation will be required to optimize such process conditions.

Example 1

Human placentas were donated after natural or planned cesarean sections with informed consent. All donations and processing were completed in accordance with FDA Good Tissue Practices (GTP) and American Association of Tissue Banks (AATB) standards. Donors were screened for medical issues, social issues, and communicable diseases, as well as infectious diseases, including human immunodeficiency virus (HIV), human T-lymphotropic virus (HTLV), hepatitis B and C, syphilis, and cytomegalovirus (CMV). Amnion with chorion, unseparated and including the intermediate layer, were isolated from the placenta, and processed. Processing involved several gentle cleaning stages followed by dehydration without freezing or high heat. The resulting dehydrated amnion/chorion was micronized using an oscillating mill, packaged without carrier according to weight (75 mg), and sent out for E-beam sterilization (Steri-tek, Fremont, CA). Micronized, dehydrated amnion/chorion was processed intact without separation of layers. The final sterilized product can be administered as a clotting/healing assist by tapping the powder directly from the vial to the open wound or using a sterile applicator to retrieve powder from the vial and transfer to the wound.

Example 2

The particulated product was produced by one steel grinding ball placed in a sterile 50 mL chamber and the chamber subsequently sealed. The chamber was placed into the cryomill (Retsch CryoMill, Haan, Germany) and run for 4 cycles of 2.5 minutes at 10 cycles per second, with 5 minutes pre-cooling. The micronized tissue was sorted using sterilized American Standard ASTM sieves, 125 μm and 300 μm. The sterile sieves were stacked with 125 μm on the bottom and 300 μm on top. The micronized material was transferred from the 50 mL chambers to the 300 μm sieve. The sieve was agitated to separate the micronized particles. If particles remained on the 300 μm sieve, those particles were ground an additional 30 seconds and resieved. Once the micronized particles were sieved, the micronized particles having particle sizes of <300 μm were collected and vialed according to weight (60 mg) and sent out for e-beam sterilization (Steri-tek, Fremont, CA).

Example 3

The sterile, micronized, dehydrated amnion/chorion/intermediate layer, which was processed without separation of any layers, was tested for growth factor content. The contents of the vial (75 mg) was transferred to one well of a 24-well plate and 500 μl of DPBS, no calcium or magnesium, was added to the well. The plate was covered and sealed with parafilm to avoid evaporation effects. The plate was then placed on a rocking plate in an incubator set to 37° C. for 72 hours. Previous studies by the inventor (unpublished) have shown that less than 72 hours results in incomplete elution from the sample and greater than 72 hours accomplished complete elution. Longer than 72 hours would not benefit the assay and would likely only promote growth factor breakdown. At 72 hours, the contents of the well are collected and centrifuged at 10,000 g for 10 minutes to clarify the sample. The supernatant was used for all assays. For all assays, five separate lots were run in duplicate. For IL-1ra, HGF, VEGFR1 determination, the supernatant was diluted 1:10 in sample diluent for BioPlex Pro singleplex cytokine assay (Bio-Rad, Hercules, California). For HA determination, samples were diluted 1:2000 in sample diluent for Hyaluronan Immunoassay (R&D Systems, Minneapolis, MN). The results from the assays (in pg/ml) were multiplied by the volume of the eluate (500 ul) to yield the total pg of each factor in the sample. The total pg was divided by the mg of sample used for the assay (75 mg) to yield the amount of each factor in each mg of the sample (pg/mg). The standard deviation was divided by the square root of the sample number (5 lots) to determine the standard error of the mean (SEM) for reporting. This provided information about the particulate can be considered if a user were to want to use 30 mg or 100 mg of particulate. Further, this method and calculation is the best way in vitro to reflect the availability of any factor measured from the particulate to the patient.

What is claimed is:

1. A sterile micronized composition prepared from intact human placental tissue that is configured for wound healing, the sterile micronized composition comprising:
(a) micronized human amnion;
(b) micronized human chorion; and
(c) micronized human intermediate spongy layer;
wherein the composition is prepared from intact placental tissue in cross-section comprising a human amnion layer, human chorion layer, and an intact human intermediate spongy layer positioned between and connecting the human amnion layer to the human chorion layer such that immediately before micronization the human amnion layer and the human chorion layer are not separated from one another;
wherein the composition is prepared without the use of exogenous enzymes; and wherein the composition comprises at least four of the following:
(a) IL-1ra ranging from $1.0\times10^2$ to $5.0\times10^4$ pg/cm2;
(b) HGF ranging from $5.0\times10^2$ to $1.0\times10^4$ pg/cm2;
(c) VEGFR1 ranging from $5.0\times10^2$ to $5.0\times10^3$ pg/cm2;
(d) HA ranging from $1.0\times10^7$ to $1.0\times10^8$ pg/cm2;
(e) GAGs; and
(f) Collagen.

2. The sterile micronized composition of claim 1, wherein the micronized human amnion comprises 10% to 20% of the total weight of the sterile micronized composition.

3. The sterile micronized composition of claim 2, wherein the micronized human chorion comprises 65% to 75% of the total weight of the sterile micronized composition.

4. The sterile micronized composition of claim 3, wherein the micronized human intermediate spongy layer comprises 10% to 20% of the total weight of the sterile micronized composition.

5. The sterile micronized composition of claim 1, wherein the composition comprises at least five of the following:
(a) IL-1ra ranging from $1.0\times10^2$ to $5.0\times10^4$ pg/cm$^2$;
(b) HGF ranging from $5.0\times10^2$ to $1.0\times10^4$ pg/cm$^2$;
(c) VEGFR1 ranging from $5.0\times10^2$ to $5.0\times10^3$ pg/cm$^2$;
(d) HA ranging from $1.0\times10^7$ to $1.0\times10^8$ pg/cm$^2$;
(e) GAGs; and
(f) Collagen.

6. The sterile micronized composition of claim 5, wherein the composition comprises each of the following:
(a) IL-1ra ranging from $1.0\times10^2$ to $5.0\times10^4$ pg/cm$^2$;
(b) HGF ranging from $5.0\times10^2$ to $1.0\times10^4$ pg/cm$^2$;
(c) VEGFR1 ranging from $5.0\times10^2$ to $5.0\times10^3$ pg/cm$^2$;
(d) HA ranging from $1.0\times10^7$ to $1.0\times10^8$ pg/cm$^2$;
(e) GAGs; and
(f) Collagen.

7. The sterile micronized composition of claim 1, wherein the micronized human amnion comprises diameters ranging from 1 µm to 500 µm.

8. The sterile micronized composition of claim 1, wherein the micronized human chorion comprises diameters ranging from 1 µm to 500 µm.

9. The sterile micronized composition of claim 1, wherein the micronized human intermediate spongy layer comprises diameters ranging from 1 µm to 500 µm.

10. The sterile micronized composition of claim 1, wherein the micronized composition is not cryofractured.

11. The sterile micronized composition of claim 1, wherein the sterile micronized composition is standardized to the weight of sterile, dehydrated, micronized placental tissue.

12. The sterile micronized composition of claim 11, wherein the sterile micronized composition is standardized by the following:

$$\frac{\text{factor assayed } (pg/\text{ml}) * (\text{ml of eluate})}{\text{mg particulate}} = pg \text{ of growth facter per mg.}$$

13. The sterile micronized composition of claim 1, wherein the micronized composition is configured for wound packing, treatment of wounds having irregular surfaces and/or peripheral boundaries, weeping wounds, dental and/or oral wounds and/or incisions, or any combination thereof.

14. A medicament comprising the composition of claim 1.

15. A therapeutic aerosol comprising the composition of claim 1 configured for intranasal and/or pulmonary administration to a subject in need thereof.

16. The therapeutic aerosol of claim 15 configured to treat pulmonary disorders, trachea disorders, and a combination thereof.

17. A therapeutic bandage comprising the composition of claim 1 configured for topical wound treatment to a subject in need thereof.

18. The therapeutic bandage of claim 17, wherein the therapeutic bandage comprises a cellulose matrix, a polymeric matrix, or a combination thereof embedded with the sterile micronized composition.

19. The therapeutic bandage of claim 18, wherein the cellulose matrix comprises a carboxyalkyl cellulose matrix or a hydroxyalkyl cellulose matrix.

20. The therapeutic bandage of claim 17, wherein the therapeutic bandage is configured to time release the sterile micronized composition to the wound over a predetermined time-period.

21. The sterilized micronized composition of claim 1, wherein the sterile micronized composition is sterilized by e-beam sterilization.

* * * * *